United States Patent

Hoskin et al.

Patent Number: 5,514,147
Date of Patent: May 7, 1996

[54] BLOOD VESSEL CLAMPS

[75] Inventors: William J. Hoskin, Harpenden; Nicholas R. Kemp, Luton, both of United Kingdom

[73] Assignee: Microsurgical Equipment Ltd., Luton, United Kingdom

[21] Appl. No.: 318,815

[22] PCT Filed: Apr. 23, 1993

[86] PCT No.: PCT/GB93/00849

§ 371 Date: Dec. 14, 1994

§ 102(e) Date: Dec. 14, 1994

[87] PCT Pub. No.: WO93/21836

PCT Pub. Date: Nov. 11, 1993

[30] Foreign Application Priority Data

Apr. 29, 1992 [GB] United Kingdom ............. 9209206

[51] Int. Cl.⁶ ............................................. A61B 17/04
[52] U.S. Cl. .......................... 606/151; 606/208; 606/158
[58] Field of Search .................................. 606/151, 158, 606/205–208

[56] References Cited

U.S. PATENT DOCUMENTS

| | | | |
|---|---|---|---|
| 4,165,746 | 8/1979 | Burgin | 606/151 |
| 4,423,729 | 1/1984 | Gray | 606/148 |
| 4,722,339 | 2/1988 | Dreier | 606/205 |
| 4,834,090 | 5/1989 | Moore | 606/148 |

FOREIGN PATENT DOCUMENTS 0218544  4/1987  European Pat. Off. .

*Primary Examiner*—Gary Jackson
*Attorney, Agent, or Firm*—Christie, Parker & Hale

[57] ABSTRACT

A blood vessel clamp has a pair of arms (2,4) each supporting a respective jaw (8,12). The arms are pivotally interconnected by a box joint (26) formed by an intermediate portion (22) of one arm (2) extending through a slot in an intermediate portion of the other arm (4) and imprisoned therein by a pivot pin (28). The internal wall of the slot is provided with a protrusion (30) at a location remote from the pin (28) such that as a part (32) of the intermediate arm (22) enters the slot during the last stages of closure of the jaws (8, 12) it engages the protrusion (30) and forces the opposite walls of the slot apart against their own resilience. This creates an increase stiffness in the joint (26) so that the jaws will remain in any desired position until a predetermined force is applied to over the stiffness whereupon they can be moved to a new position.

13 Claims, 3 Drawing Sheets

BLOOD VESSEL CLAMPS

BACKGROUND

The present invention relates to blood vessel clamps.

Blood vessel clamps are used in surgical procedures to reduce or cut off the blood flow or supply in veins or arteries.

Such clamps, known for example from EP-A-218544, conventionally consist of scissor-like structures having mating gripping jaws instead of cutting blades. In addition a ratchet mechanism is provided on each arm. The two ratchet mechanisms engage during the last stages of approach between the two jaws so as to prevent the jaws from moving apart. Each ratchet mechanism is in the form of a projection extending from one arm of the clamp at a position adjacent the finger hole, towards the other arm of the clamp. The leading edge of each arm is so profiled that when the two edges engage they are displaced away from one another in a direction normal to the direction of motion so that the lower surface of one projection can then ride over the upper surface of the other projection, as the two projections continue to move towards one another. The two facing surfaces of the projections are each provided with a sawtooth profile. The saw teeth interlock with one another and prevent the two projections moving away from one another but allow continued movement towards one another to increase the number of the teeth of the two portions interlocking with one another. Thus a series of spaced discrete locking positions is achieved as the two jaws move together. To release the teeth from one another, the two projections must be first moved towards one another to a position intermediate the adjacent locking positions and then displaced in perpendicular direction to cause the two sets of teeth to disengage one another before the arms of the clamp can be moved apart.

Such clamps have serious disadvantages. In use when a blood vessel is held between the jaws, the blood flow is monitored as the jaws are closed. When the blood flow reaches the desired level or stops, the jaws usually need to be closed further to reach the nearest locking position. Furthermore, to unlock the jaws, the jaws have to be closed tighter still before the ratchet mechanisms can be disengaged. This results in a greater pressure being applied to the vessel than is necessary and this can lead to damage of the vessels particularly if there has been a build up inside the vessel of calcium or other material. Still further, the crushing or fragmentation of such a build up may mean that the fragments are subsequently released into the blood supply system with the consequent danger of a thrombosis or blockage in another part of the system.

SUMMARY OF THE INVENTION

It is an object of the present invention to provide an improved blood vessel clamp.

According to the present invention there is provided a blood vessel clamp comprising a pair of arms providing a pair of jaws, means pivotally connecting the arms together to enable the jaws to move angularly into and out of mating engagement with each other, and means for creating a predetermined stiffness against relative angular movement at least during the final approach of the jaws before they engage one another, to hold the jaws in any desired position in said final approach, until released in response to a predetermined pressure sufficient to overcome the stiffness.

BRIEF DESCRIPTION OF THE DRAWINGS

A blood vessel clamp embodying the present invention will now be described, by way of example, with reference to the accompanying diagrammatic drawings in which.

DETAILED DESCRIPTION OF PREFERRED EMBODIMENTS

Figure 1:
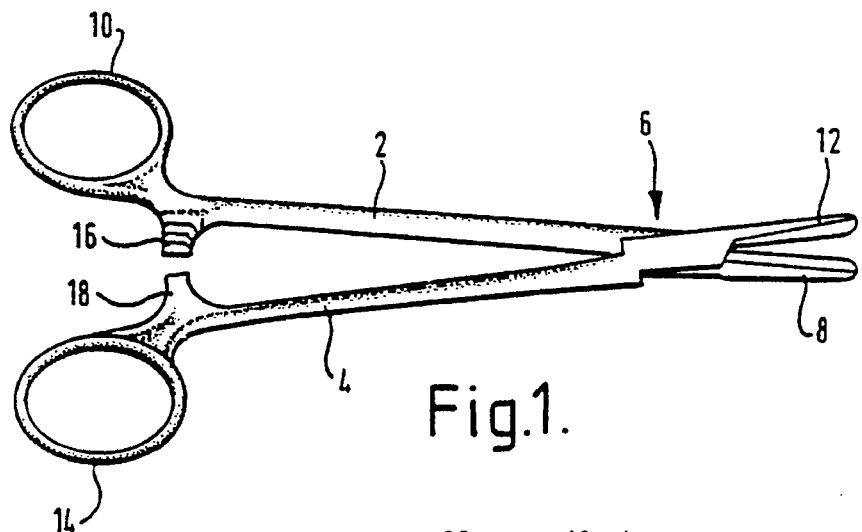
FIG. 1 is a plan view of a previously proposed blood vessel clamp.

FIG. 1 shows a previously proposed stainless steel blood vessel clamp comprising a pair of arms 2,4 interconnected by a box joint 6. The arm 2 has a jaw 8 at one end and a finger hole 10 at the other end. The arm 4 has a jaw 12 at one end and a finger hole 14 at the other end. The jaws 8,12 have facing surfaces which cooperate to grip a blood vessel. The facing surfaces are roughened to improve their gripping action.

Each arm 2,4 carries a respective projection 16,18 adjacent the finger holes. The projections carry mating ratchet teeth which can lock the arms against movement apart, in a series of discrete spaced positions. The disadvantages of this type of clamp have been previously set out.

Figure 3:
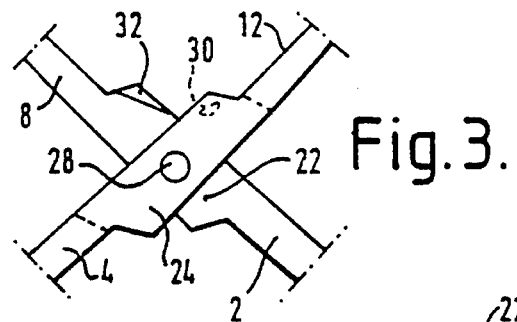
FIG. 3 is a fragmentary plan view of the box joint of the clamp of FIG. 2.
Figure 4:
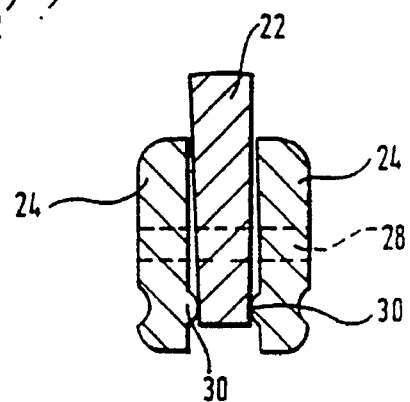
FIG. 4 is a cross-section through the box joint of FIG. 3.
Figure 2:
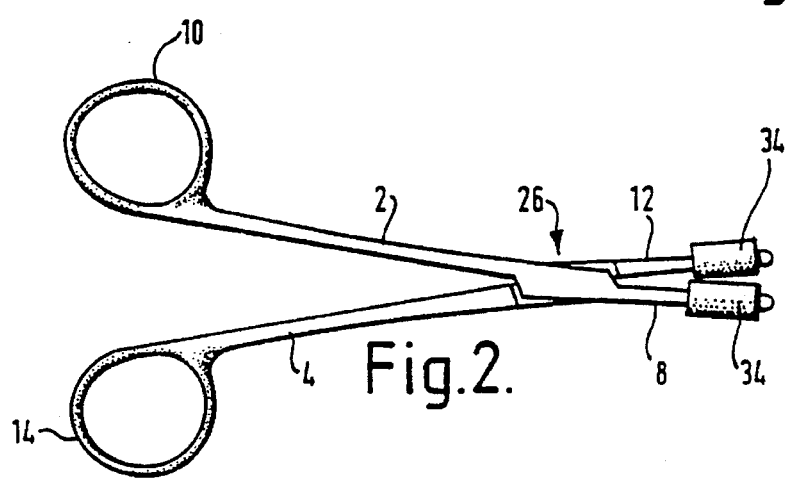
FIG. 2 is a plan view of a plan view of the blood vessel clamp embodying the invention.

FIGS. 2 to 4 show a clamp embodying the invention. In FIGS. 2 to 4 parts similar to those in FIG. 1 are similarly referenced. The box joint 26, shown in FIG. 2, comprises a rectangular slot in an intermediate portion 24 of the arm 4 which is engaged by an intermediate portion of the arm 2; which portion is of rectangular cross-section. A pivot pin 28 traverses the intermediate portions 22,24 to pivotally link the two arms together. The intermediate portion 22 of the arm 4 is normally a clearance fit within the slot of the intermediate portion 24. However, a protrusion 30 is formed on each of the two opposite internal faces of the slot at a location remote from the pivot 28. Thus, as a part of the intermediate portion 22 remote from the pivot 28 enters the slot during the action of closing the jaws it engages the protrusions 30 (see FIG. 4). Since the distance between the protrusions is slightly shorter than the thickness of the portion 22, the walls of the slot are slightly forced apart against their own resilience and further relative angular displacement between the two arms in the same sense becomes stiff. The stiffness is sufficient to hold the two arms in any relative position. Thus, if a blood vessel is gripped between the jaws 8,12, the pressure in the blood vessel is more likely to rupture the vessel itself rather than force the two jaws apart.

The leading edge 32 of the intermediate portion 22 may be made so that opposite faces thereof are slightly convergent, sloping relative to one another by at least ½° or advantageously 1°, so that the stiffness of the joint increases progressively as the intermediate portion 22 progressively engages the protrusions 30. The protrusions 30 may be produced by placing a former of tool steel and having a through hole in the slot and placing the arm 4 in a press so as to force material from the walls of the slot to project into the through hole.

Sleeves 34 of silicon rubber are threaded onto the jaws 8,12 so that the load applied by the jaws on the blood vessel is distributed and damage to the outer surface of the vessel is minimised.

Figure 5:
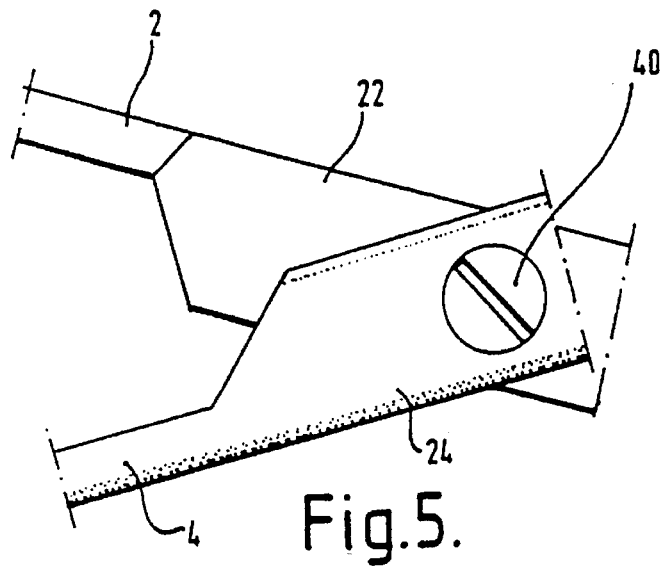
FIG. 5 is a fragmentary plan view showing an alternative joint for the clamp of FIG. 2.
Figure 6:
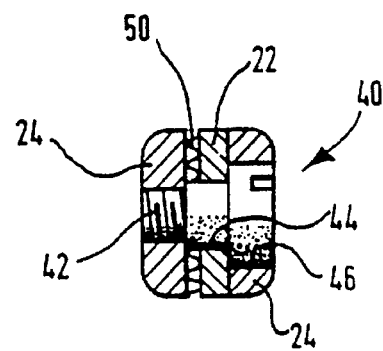
FIG. 6 is a cross-section through the joint of FIG. 5.

FIGS. 5 and 6 show a modified box joint for the clamp of FIGS. 2 to 4. In FIGS. 5 and 6 parts similar to those in FIGS. 3 and 4 are similarly referenced. As can be seen the pivot is in the form of a bolt 40 having a screwthreaded end portion 42, an enlarged neck 44, and a head 46. As viewed in FIG. 6, one wall of the slot has a screwthreaded opening which is sized to screwthreadedly engage the end portion 42 of the bolt 40. The intermediate portion 22 of the arm 2 has an opening sized to receive the enlarged neck 44. The other wall of the slot has an opening therein sized to receive the head 46. The head 46, being larger than the neck 44, bears against the adjacent face of the intermediate portion 22. A wavy resilient spring washer 50 encircling the threaded end portion 42 lies between the intermediate portions 22,24 to urge the intermediate portion 22 against the head 46. By tightening the bolt 40 against the resilience of the spring washer, the stiffness of the box joint can be adjusted. The stiffness will hold the jaws of the clamp in any position in which they are left.

Figure 7:
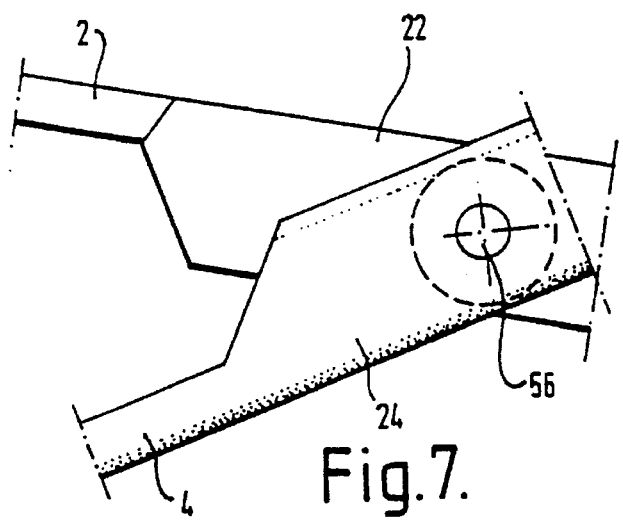
FIG. 7 is a fragmentary plan view of another alternative joint for the clamp of FIG. 2.
Figure 8:
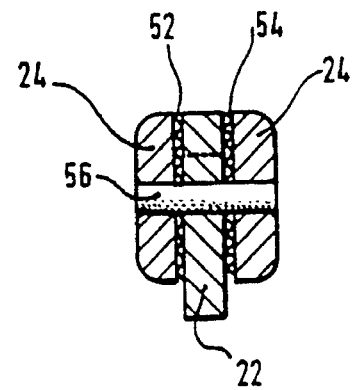
FIG. 8 is a cross-section through the joint of FIG. 7.

In the modified box joint shown in FIGS. 7 and 8, two wavy resilient spring washers 52,54 are provided one on each side of the intermediate portion 22. In place of the bolt of FIG. 6, a rivet 56 is used. As with the arrangement of FIGS. 5 and 6, the box joint is stiff and this stiffness enables the jaws of the clamp to be held in any position to which it is moved.

Figure 9:
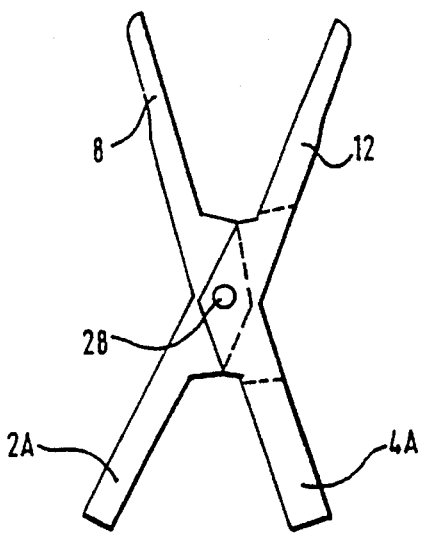
FIG. 9 is a plan view of another form of clamp.

The blood vessel clamps described may be made of stainless steel, or of titanium for example.

Where blood vessels need to be clamped in confined spaces the clamps shown in FIG. 9 can be used. Instead of the full arms 2,4 of the other embodiments, vestigial arms 2A,4A are provided. Also the box joint used is not the usual cross-over type but one in which the arm 2A and its corresponding jaw 8 lie on the same, rather than opposite sides, of the pivot.

A tool (not shown) may be used to grip the jaws 8,12 to move from together to clamp a desired blood vessel. The tool is then disengaged leaving the clamp in place. To release the clamping action, the same tool is used to grip the vestigial arms 2A,4A to move the arms together. As the arms move together the jaws 8,12 open to release the vessel.

The stiffness in the box joint may be created in any of the ways described in conjunction with FIGS. 2 to 8. Instead the mating surfaces of the two arms 2A,4A within the box joint are coated with tungsten carbide, making a tight joint to create a wear resistant stiffness against relative angular displacement.

The blood vessel clamps described provide a continuously variable clamping action in contrast to the stepped clamping action of the previously proposed clamps.

Figure 10:
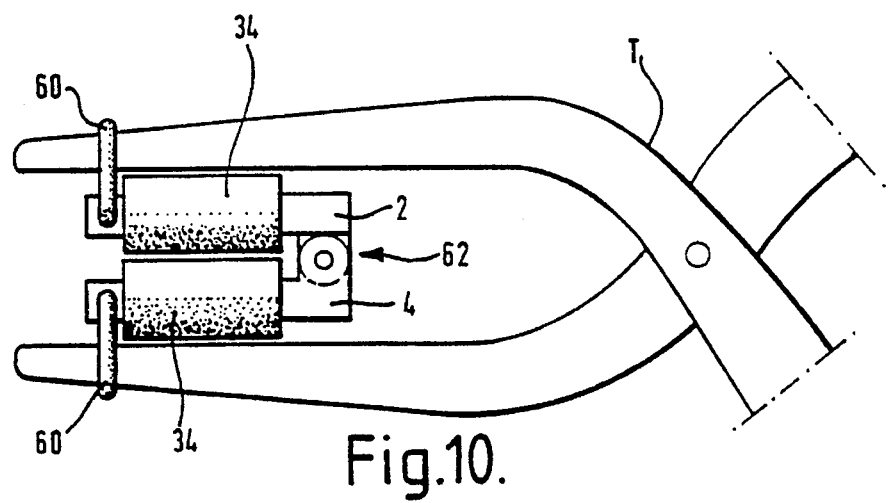
FIG. 10 is a side view of another form of clamp and a tool for operating it.
Figure 12:
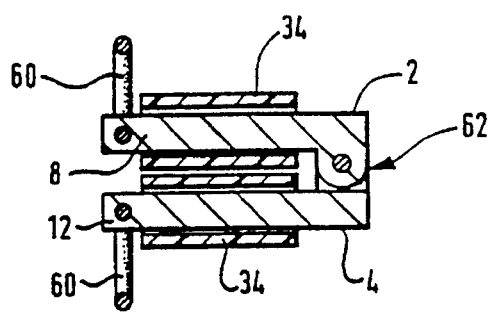
FIG. 12 is a vertical cross-section through the clamp of FIG. 10.
Figure 11:
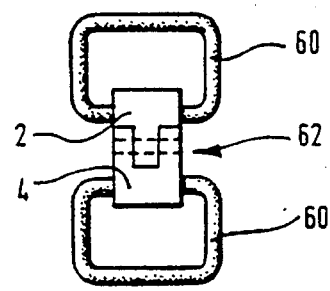
FIG. 11 is an end view of the clamp of FIG. 10.

The embodiment of FIGS. 10 to 12 is of particular advantage where a large number of clamps may be needed in a confined space. In this embodiment the arms 2,4 are very much shortened and in essence provide only the jaw portions 8,12 thereof. The arms are pivotally connected together at their first ends by a simple hinge 62. The mating surfaces of the hinge form a tight fit and may be coated with a layer of tungsten carbide. Alternatively, pivotal connections such as the box joints described in relation to previous embodiments may be employed.

A pair of rings 60 are pivotally mounted at the second ends of the arms 2,4 remote from the hinge 62 about axes parallel to the hinge axis. The pivotal mounting of the rings is again fairly stiff so that they will stay in any desired position. As can be seen in FIG. 10, the rings 60 enable the clamp to be engaged by a tool T, e.g. in the form of pincers. The tips of the limbs of tool T pass through the rings 60 such that operation of the pincers leads to operation of the clamp. When the clamp is in place on a blood vessel the tool T can be removed until it is desired to remove the clamp. The jaws of the clamp are both surrounded by a silicon rubber sleeve 34. The sleeves 34 are not shown in FIG. 11 for the sake of clarity.

We claim:

1. A blood vessel clamp comprising a pair of arms, a pair of jaws provided on the arms and having facing surfaces which co-operate to grip a blood vessel, a pivotal connection for pivotally connecting the arms such that they cross over one another at a position intermediate their ends and enabling the jaws to move angularly into and out of mating engagement with each other, characterised in that means are provided for increasing the stiffness against relative angular movement to at least a predetermined value during the final approach of the jaws before they engage one another, to hold the jaws more tightly in any desired position in said final approach, until released in response to a predetermined pressure sufficient to overcome the stiffness.

2. A clamp according to claim 1, wherein said pivotal connection means comprises a box joint in which an intermediate portion of one arm extends into an elongate slot in an intermediate portion of the other arm and including a common pivot pin extending through both said intermediate portions.

3. A clamp according to claim 2, wherein the stiffness increasing means comprises a protrusion extending from one of said intermediate portions positioned to engage the other said intermediate portion only during said final approach travel to force the walls of the slot apart against their own resilience.

4. A clamp according to claim 3, wherein the surface of said other portion which is engaged by said protrusion is inclined relative to the surface supporting the protrusion in a sense such that the stiffness increases progressively as the jaws approach on another.

5. A clamp according to claim 3, wherein said relative inclination is at least ½°.

6. A clamp according to claim 2, wherein one arm and its corresponding jaw are located on one side of the slot and the other arm and its corresponding jaw are located on the opposite side of the slot.

7. A clamp according to any preceding claim, wherein each arm has a finger hole at an end thereof opposite the jaw.

8. A blood vessel clamp comprising a pair of arms, a pair of jaws provided on the arms and having facing surfaces which co-operate to grip a blood vessel, a pivotal connection for pivotally connecting the arms at their first ends and enabling the jaws to move angularly into and out of mating engagement with each other, and means for creating a predetermined stiffness against relative angular movement at least during the final approach of the jaws before they engage one another, to hold the jaws in any desired position in said final approach, until released in response to a predetermined pressure sufficient to overcome the stiffness.

9. A clamp according to claim 8, wherein means are provided on the arms for enabling the clamp to be engaged by a tool for opening and closing the clamp.

10. A clamp according to claim 9, wherein the means enabling the clamp to be engaged by a tool comprise a pair of rings each pivotally mounted at the second end of a respective one of the arms remote from the pivotal connection about an axis parallel to that of the pivotal connection.

11. A clamp according to claim 9 or claim 10, wherein the pivotal connection comprises a simple hinge.

12. A clamp according to claim 10, wherein the mating surfaces of the pivotal connection are coated with a layer of tungsten carbide.

13. A clamp according to claim 8, including a silicon rubber sleeve on each said jaw.

* * * * *